(12) United States Patent
Iwaki et al.

(10) Patent No.: US 7,425,434 B2
(45) Date of Patent: Sep. 16, 2008

(54) GENE ENCODING CYCLODODECANONE MONOOXYGENASE

(75) Inventors: Hiroaki Iwaki, Montreal (CA); Yoshie Hasegawa, Osaka (JP); Peter C. K. Lau, Kirkland (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 11/717,247

(22) Filed: Mar. 13, 2007

(65) Prior Publication Data

US 2007/0184531 A1    Aug. 9, 2007

Related U.S. Application Data

(62) Division of application No. 10/489,883, filed as application No. PCT/CA02/01434 on Sep. 18, 2002, now Pat. No. 7,217,559.

(60) Provisional application No. 60/323,129, filed on Sep. 19, 2001.

(51) Int. Cl.
  *C12N 1/21* (2006.01)
  *C12N 9/02* (2006.01)
  *C12N 15/74* (2006.01)
  *C12P 21/06* (2006.01)
  *C12P 1/68* (2006.01)
  *C07H 21/04* (2006.01)

(52) U.S. Cl. .................... 435/189; 435/6; 435/69.1; 435/320.1; 435/252.33; 536/23.2

(58) Field of Classification Search .................. 435/189, 435/6, 69.1, 320.1, 252.3; 530/350; 536/23.2
See application file for complete search history.

(56) References Cited

FOREIGN PATENT DOCUMENTS

| WO | WO 01/42436 A2 | 6/2001 |
| WO | WO 01/42436 A3 | 6/2001 |

OTHER PUBLICATIONS

Kostichka et al., "Cloning and characterization of a gene cluster for cyclododecanone oxidation in *Rhodoccocus ruber* SCI", Journal of Bacteriology, 183: 6478-6486 (2001).
Schumacher et al., "Degradation of alicyclic molecules by *Rhodococcus ruber* CD4", Appl Microbiol Biotechnol 52: 85-90 (1999).
Willets, "Structural studies and synthetic applications of Baeyer-Villiger monooxygenases", Trends in Biotechnology 15: 55-62 (1997).
Sambrook, Joseph et al.: "Molecular Cloning: A Laboratory Manual" Second Edition, Cold Spring Harbor Laboratory Press, 1989, pp. 1.101-1.104.

*Primary Examiner*—Rebecca E. Prouty
*Assistant Examiner*—Iqbal Chowdhury
(74) *Attorney, Agent, or Firm*—Nixon Peabody LLP

(57) ABSTRACT

The invention relates to a new strain of *Pseudomonas putida* (designated as HI-70) and to the isolation, cloning, and sequencing of a cyclododecanone monooxygenase-encoding gene (named cdnB) from said strain. The invention also relates to a new cyclododecanone monooxygenase and to a method of use of the cyclododecanone monooxygenase-encoding gene.

3 Claims, 3 Drawing Sheets

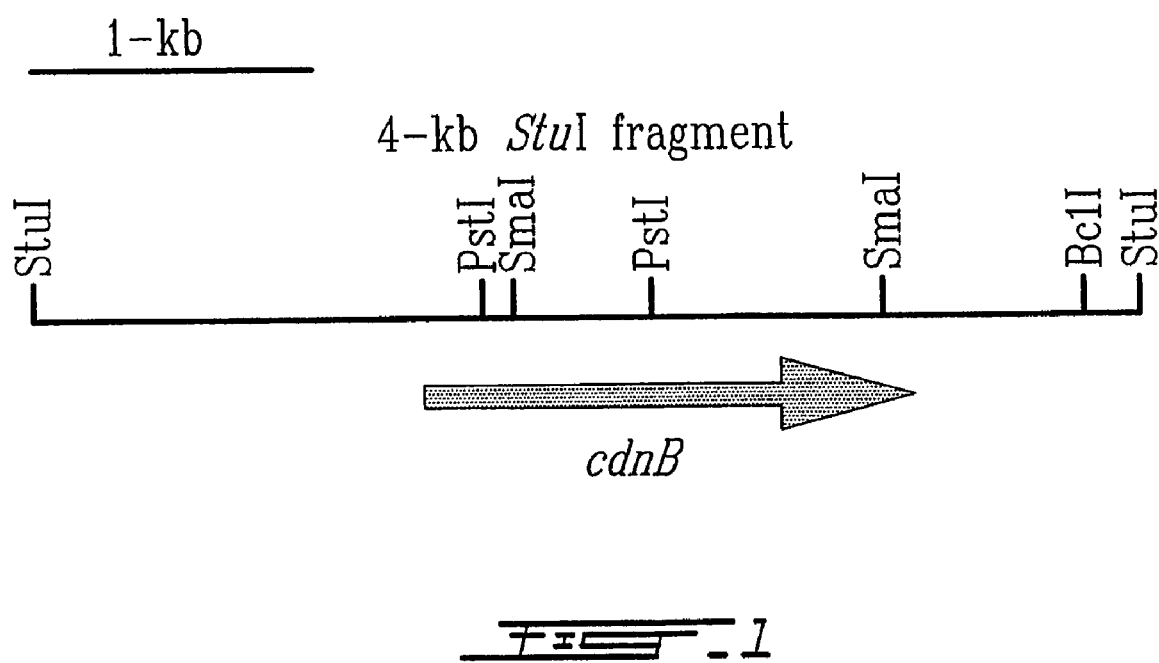

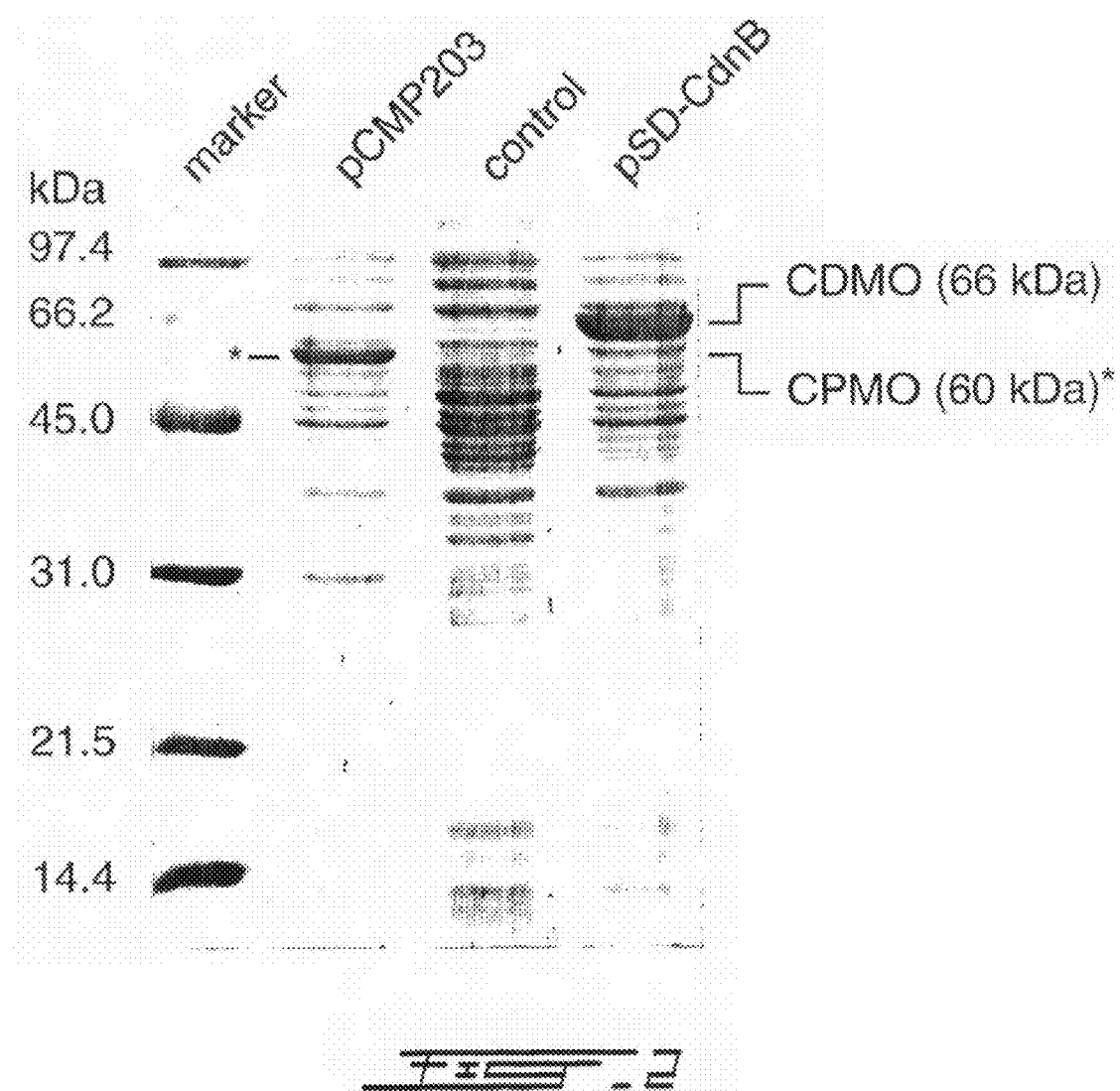

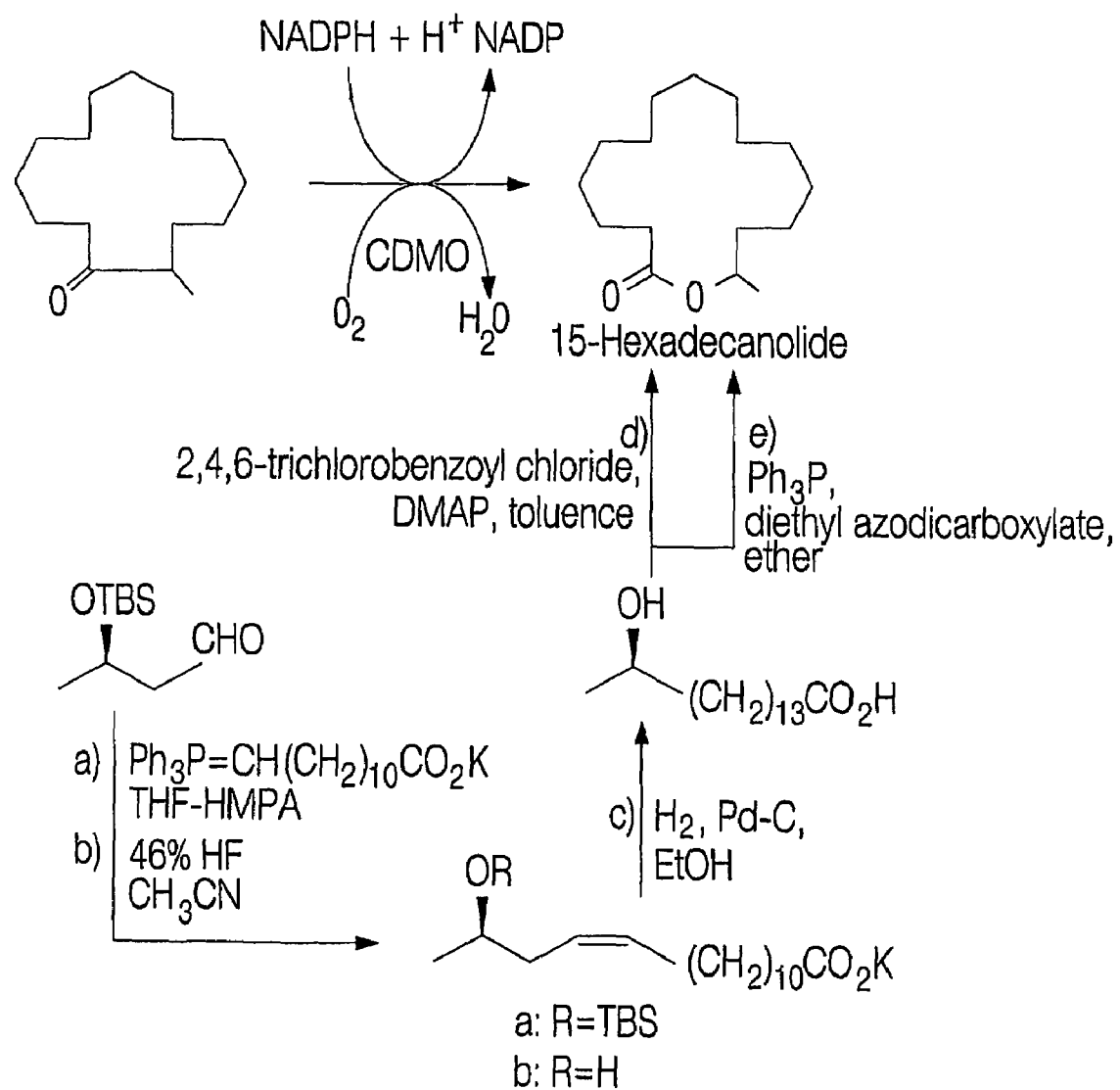

US 7,425,434 B2

GENE ENCODING CYCLODODECANONE MONOOXYGENASE

CROSS-REFERENCE TO RELATED APPLICATIONS

This application is a Divisional of U.S. application Ser. No. 10/489,883, now U.S. Pat. 7,217,559, which is a 371 of PCT/CA02/01434 filed on Sep. 18, 2002, which claim benefit of Application No. 60/323,129 filed on Sep. 19, 2001.

BACKGROUND OF THE INVENTION (a) Field of the Invention

The invention relates to a new strain of *Pseudomonas putida* (designated as HI-70) and to the isolation, cloning, and sequencing of a cyclododecanone monooxygenase-encoding gene (named cdnB) from said strain.

(b) Description of Prior Art

Enzymatic Baeyer-Villiger monooxygenases (BVMO) in general are flavoproteins that can mimic the classical (100-year old) organic Baeyer-Villiger oxidations of a wide variety of ketones to lactones, many of which are valuable chiral building blocks. The deployment of microbial BVMOs in the synthesis of natural products such as lipoic acid and Baclofen, an antagonist of gamma-aminobutyric acid (better known as GABA) demonstrates the power and utility of this group of enzymes (Kelly, D. R. et al. 1998 in *Biotransformation I, pp.* 535-587). The use of enzymes as bio-reagents has the advantages of specificity, waste minimization and environmental friendliness. In a world where sustainable development is an increasing important issue, the use of biocatalysts to drive synthesis of essential products in various industrial applications is becoming a matter of priority choice for the Organisation For Economic Co-Operation And Development (OECD).

To date, there is a limited list of microorganisms (bacteria and fungi) that have been shown to produce BVMOs (Stewart, J. D. *Curr. Org. Chem.* 2:195-216, 1998; Kelly et al. supra; Schumacher J. D. and Fakoussa, R. M. *Appl. Microbiol. Biotechnol.* 52: 85-90, 1999; Kamerbeek, N. M. et al. *Eur. J. Biochem.* 268:2547-2557, 2001). A few BVMO-encoding genes have been cloned encoding products with varying substrate specificities (Iwaki, H. et al. *Appl. Environ. Microbiol.* 65:5158-5162, 1999; Cheng, Q. et al. *J. Bacteriol.* 182:4744-4751, 2000; Brzostowicz P. C. et al. *J. Bacteriol.* 182: 4241-4248, 2000; Kamerbeek, N. M. et al. *Eur. J. Biochem.* 268:2547-2557, 2001).

It would be highly desirable to be provided with a new soil microorganism capable of using cyclododecanol and cyclododecanone (12-membered ring compounds) as sole carbon source for growth and energy.

It would also be desirable to be provided with the isolated DNA sequence that allows the above microorganism to use cyclododecanol and cyclododecanone (12-membered ring compounds) as sole carbon source for growth and energy.

SUMMARY OF THE INVENTION

One aim of the present invention is to provide a new soil microorganism capable of using cyclododecanol and cyclododecanone (12-membered ring compounds) as sole carbon source for growth and energy.

Another aim of the present invention is to provide the isolated DNA sequence that allows the above microorganism to use cyclododecanol and cyclododecanone (12-membered ring compounds) as sole carbon source for growth and energy.

In the present invention, it was found that the DNA that allows the above microorganism to use cyclododecanol and cyclododecanone (12-membered ring compounds) as sole carbon source for growth and energy is a cyclododecanone monooxygenase.

Accordingly, another aim of the present invention is to provide the amino acid sequence of the cyclododecanone monooxygenase.

In accordance with the present invention, there is provided a new soil microorganism, identified as *Pseudomonas putida* strain HI-70, that is capable of using cyclododecanol and cyclododecanone (12-membered ring compounds) as sole carbon source for growth and energy. The microorganism has a gene coding for a cyclododecanone monooxygenase. To date, it is believed that the cloned cdnB gene encoding the cyclododecanone monooxygenase (CDMO) of strain HI-70 is the first of its kind by sequence and substrate specificity towards cycloketones with ten ring members or above. Also, over-expression of the cdnB gene in *E. coli* provides a rich source of this recombinant enzyme for use in various biotransformations.

In accordance with the present invention there is also provided an isolated DNA encoding a cyclododecanone monooxygenase (CDMO) having an amino acid sequence as set forth in SEQ ID NO:8, or an enzymatically active portion thereof.

Further in accordance with the present invention, there is provided an isolated DNA encoding a cyclododecanone monooxygenase (CDMO) or an enzymatically active portion thereof, the isolated DNA being characterized by the ability to hybridize specifically with the complement of the DNA represented in SEQ ID NO:7 under stringent hybridization conditions.

In one embodiment of the invention, there is provided an isolated DNA coding for a cyclododecanone monooxygenase (CDMO), and containing:

(a) a nucleic acid sequence as set forth in SEQ ID NO:7;

(b) a sequence corresponding within the degeneracy of the genetic code to said nucleic acid sequence and coding for a cyclododecanone monooxygenase; or (c) a sequence hybridizing under stringent conditions with the complement of the sequence from (a) or (b), and still coding for cyclododecanone monooxygenase (CDMO).

The present invention further provides an isolated DNA encoding a cyclododecanone monooxygenase (CDMO), or an enzymatically active portion thereof, said isolated DNA having SEQ ID NO:7.

In one embodiment of the present invention, the enzymatically active cyclododecanone monooxygenase (CDMO) of the present invention can be encoded by an expression vector that comprises a DNA as defined above. The expression vector may comprises one or more copies of the DNA that codes for the enzymatically active cyclododecanone monooxygenase (CDMO). The expression vector may either be a prokaryotic or eukaryotic vector. The vector may in some embodiments as well be a plasmid, which plasmid may then be used to transformed host cells or to be incorporated into these host cells.

Accordingly, the present invention further provides a biologically functional plasmid or viral DNA vector that contains a DNA as defined above.

Still in accordance with the present invention, there is also provided a cell transformed with a heterologous DNA expression construct encoding an enzymatically active cyclododecanone monooxygenase (CDMO), said construct comprising an isolated DNA as defined in any one of claims 1 to 5, said cell once transformed expressing said CDMO. The cell may be a prokaryotic cell. The cell may also be an *E. coli* cell.

Further in accordance with the present invention, there is provided a cyclododecanone monooxygenase (CDMO) having an amino acid sequence as set forth in SEQ ID NO:8.

Still in accordance with the present invention, there is also provided a method for growing cells in vitro in presence of cyclododecanol or cyclododecanone as sole source of carbon, said method comprising the steps of:
(a) transforming a cell with either an expression vector as defined herein with a biologically functional plasmid or viral DNA vector as defined herein; and
(b) growing the cell of step a) under suitable conditions in a medium containing cyclopentanol or cyclododecanone as a sole source of carbon.

BRIEF DESCRIPTION OF THE DRAWINGS

FIG. 1 illustrates a genetic map of a clone containing the 4.2-kb Bcll and 4.0-kb Stul inserts was screened by colony hybridization using the PCR product as a probe;

FIG. 2 is a photograph of a Coomassie Brilliant Blue stained protein gel after polyacrylamide gel electrophoresis of over-expressed CDMO in *E. coli* compared to control samples and a molecular size standard; and FIG. 3 illustrates a Five-step chemical synthesis of hexadecanolides versus a single step CDMO-catalysed reaction.

DETAILED DESCRIPTION OF THE INVENTION

In accordance with the present invention, there is described the isolation of a new strain of *Pseudomonas putida* (designated as strain HI-70) that is capable of utilising cyclododecanone or cyclododecanol as a sole carbon source, the cloning and sequencing of a cyclododecanone monooxygenase-encoding gene (named cdnB) from said strain, the expression of said cdnB gene in a heterologous system (*E. coli*), and activity assays of the said enzyme. The specificity spectrum and utility of the CDMO of the present invention for the oxidation of large ring-membered moncyclic ketones (with at least 10, preferably 12 or more rings) to lactones, something that no other enzymes are known to do, was determined with these assays.

Isolation of a New Strain of *Pseudomonas putida* Encoding a Cyclododecanone Monooxygenase (CDMO)

An organism was isolated from a soil sample from Osaka, Japan by selective enrichment by using a minimal salts medium (MSM), pH 7.0, containing cyclododecanone (1.0 g per liter). It was maintained on either liquid or solid minimal salts medium containing cyclododecanone as the sole carbon source. MSM contained (per liter of distilled water) 1.0 g of $NH_4NO_3$, 1.5 g of $KH_2PO_4$, 1.5 g of $Na_2HPO_4$, 0.5 g of $MgSO_4.7H_2O$, 0.01 g of $CaCl_2.2H_2O$, 0.005 g of $FeSO_4.7H_2O$, 0.002 g of $MnSO_4.4H_2O$ and 0.05 g of $ZnSO_4.7H_2O$. The isolate was identified and classified as a member of *P.putida* by NCIMB Japan Co. Ltd. (Shizuoka, Japan). This strain was designated strain HI-70.

Cloning of the *Pseudomonas putida* HI-70 CDMO-Encoding Gene

*Pseudomonas putida* HI-70 was grown at 30° C. in Luria-Bertani (LB) broth, or minimal salt medium (MSM), pH 7.0, containing 0.3% of cyclododecanone. Agar was added to 1.5% per plate. Genomic DNA of strain HI-70 was prepared by the Marmur method. Based on two conserved regions (WY/HWNR/CYP (SEQ ID NO:1 and ATGFDA (SEQ ID NO:2)) of BVMOs (CHMO of *Acinetobacter* sp. NCIMB 9871, CPMO of *Comamonas testosteroni* NCIMB9872, CHMO of *Rhodococcus maris* HI-31 and STMO of *Rhodococcus rhodochrous* IFO 3338), two degenerated PCR primers (5'-TGGYAYTGGAAYHGITAYCC -3' (SEQ ID NO:3) and 5'-GCRTCRAANCCNGTIGC-3' (SEQ ID NO:4), corresponding to amino acids of *Acinetobacter* CHMO 46-52 and 377-382, respectively; I=inosine; N=T,C,A or G; R=A or G; Y=C or T; H=A,C or T) were synthesized to amplify a ca 1-kb product from total DNA prepared from strain HI-70.

The PCR amplification was performed in a Perkin Elmer-Model 2400 Thermal Cycler™ and the amplification conditions were 94° C. for 1 min, 50° C. for 1 min, and 72° C. for 2 min, for 30 cycles. Before using the amplified product as a gene probe its nucleotide sequence was confirmed. Nucleotide sequencing was determined by the Taq DyeDeoxy terminator cycle sequencing kit and the ABI Prism 310 Genetic Analyzer (Perkin Elmer).

The two special sets of primers were designed for the first time ever for use in a PCR amplification of a potential BVMO-encoding gene. This strategy took advantage of the fact that blocks of conserved amino acid sequence among proteins of evolutionary distinct origins but with a common biological activity or function would be an invaluable source of information for gene cloning. The successful cloning of cdnB described in the present application validates this approach. The amplified gene productgenerated by each of the two sets of primers were used as probes. This designed set of probes is expected to be useful for the cloning of any other BVMO-related genes.

To clone the CDMO-containing gene, amplified fragment was labeled by the digoxigenin-11-UTP system according to manufacturer's instructions (Boehringer Mannheim GmbH) and used to probe a Southern hybridization of strain HI-70 genomic DNA digested with various restriction enzymes (BamHI, Bcll, EcoRI, HindIII, Kpnl, NheI, Pstl, Sa/l, Sphl, Stul and Xbal). As a result, a single hybridizing band of ca 4.2-kb Bcll fragment and 4.0-kb Stul fragment was obtained. Hybridization conditions were carried out at 68° C. according to Sambrook et al. Subsequently, a purified 3.5- to 4.5-kb size fraction of Bcll or Stul-cut total DNA separated on a 0.8% agarose gel was ligated to *E. coli* plasmid pUC19, which had been linearized and dephosphorylated.

A clone containing the 4.2-kb Bcll and 4.0-kb Stul inserts was screened by colony hybridization using the PCR product as a probe; these recombinant plasmids were designated pCD200 (4.2-kb Bcll) and pCD100 (4.0-kb Stul). A genetic map is illustrated in FIG. 1 has been established.

Expression of cdnB Gene in *E. coli*

Two primers of the following sequence (SEQ ID NO:5 and SEQ ID NO:6) were synthesized to amplify the cdnB gene and the resultant 1.8-kb DNA fragment was cloned in the pSD80 plasmid to yield pCD101. Plasmid pSD80 is a third generation derivative of the commercially available pKK223-3 vector (Pharmacia) that contains a tac promoter upstream of the multiple cloning site (MCS), an unc terminator sequence downstream of the MCS, and laclq elsewhere on the plasmid. The primers were: 5'-CGGAATTCATGAGT-CAGCTAATTCAAGAGC-3' (SEQ ID NO:5) and 5'CGGAATTCAATCAACGCTTGCGCTGCTG-3' (SEQ ID NO:6) with built-in EcoRI restriction sites, to facilitate cloning at the compatible sites (EcoRI) of the pSD80 vector. Pfu polymerase was used and the amplification conditions were 94° C. for 1 min, 50° C. for 1 min, and 72° C. for 3 min, for 30 cycles. The amplified DNA fragment was purified from an agarose gel and digested with EcoRI.

One of the resulting recombinant plasmids was designated pCD101. By DNA sequencing, it was established that no mutation had been introduced in the cdnB gene during PCR amplification.

The DNA sequence of the cdnB gene was determined to be as follows:

```
                                               (SEQ ID NO:7)
atgagtcagc taattcaaga gccggccgag gctggggtaa          60
cgtcgcagaa agtttccttc gatcatgtgg cgcttcgcga aaaatatcgt caggagcgcg         120
acaagcgctt gcgtcaggac ggccaagagc aatatctgga agtcgccgtc acatgtgacg         180
aataccctgaa agacccctat gccgatccga tcgtgcgtga tccggtggtg cgcgagaccg         240
acgtgttcat catcggtggc ggtttcggtg gtctgttggc tgcggtacgc ctgcagcaag         300
caggcgttag cgattatgtg atggttgagc gcgccggtga ctatggcggc acctggtact         360
ggaaccgcta cccgggggcg cagtgcgaca tcgagtcgta tgtctacatg cccttgctcg         420
aagaaatggg ttacataccg accgagaagt acgccttcgg tacgagatc ctcgagtact          480
ccagatcaat cggccgcaaa tttggcttgt acgagcgcac ctacttccag actgaagtga         540
aggatctgag ctgggacgat gaagcggccc gctggcgcat taccaccgac gcgggcgaca         600
agttcagcgc gcgcttcgtg tgcatgtcca ccgccccttt gcagcggccc aaactgcccg         660
gcatcccagg tatcacgtcc ttcaagggcc actccttcca caccagtcgc tgggactact         720
cctataccgg cggcgatcag accggcaacc tggaaggttt gaaagacaag cgcgtggcca         780
tcatcggtac cggcgccacc tcaatccagg ctgtgccaca cctggcggcc tatgcccaag         840
agctgtatgt catccagcgc acgccaattt ccgtgggctt ccgtggcaac aagccgactg         900
atcctgaatg ggccaagagc ctgcagccgg gttggcagca agcgcgtatg gacaacttca         960
atgcgatcac ccacggcatg ccggtcgatg tcgatctggt ccaggacagc tggaccaaga        1020
tcttcggcga aatcggcgtt tttctgggtt ccgatggcag ccgtgcgcag atggtcgact        1080
tccagttgat ggagcaaatc cgcgccccgcg tcgatcagga agtcaaggat ccggccaccg        1140
ctgagtcgct caagccttac tacaacatca tgtgtaagcg tccgggcttc catgacagtt        1200
atctgccctc cttcaacaag cccaatgtca ccctggtcga tacccaaggc gctggtgttg        1260
agcgcatcac cgaaaaggc ctggtggtca acgccgcga atatgaagtc gactgcctga        1320
tctacgccca cggcttcgag taccagacca agttgtcgcg ccgcaatggc tacgaaatcc        1380
acgggcgcaa tggccagccg ctgagtgaca agtggaaaga cggcctgtcc acactgtggg        1440
gctaccacat tcgtgacttc ccgaactgct tcatccttgg caatggtcag tctgcggtaa        1500
caccgaactt cactcacatg ctcaacgaag ctggcaagca tgtggcctat gtggtcaagc        1560
actgcctgga cgagcgcgtc gatgtcttcg agccgaccgc agaggctgag caggcgtggg        1620
ttgaccacgt catgtcgttc gctgggatca agcagcaata cgaccgcgag tgcaccccga        1680
gttactacaa caacgaaggc caggtgaacg acgttgcgct gaccccgcaca acttctaccc        1740
gggcggtgcg gtcgcttata aacattctgc gggagtggcg agagaagggc gatttcgcgc        1800
agttccagca gcgcaagcgt tga                                                1803
```

From the above sequence, the amino acid sequence of the CDMO of the present invention was determined to be as follows:

```
                                            (SEQ ID NO:8)
Met Ser Gln Leu Ile Gln Glu Pro Ala Glu Ala Gly
 1               5                  10

Val Thr Ser Gln Lys Val Ser Phe Asp His Val Ala
            15                  20

Leu Arg Glu Lys Tyr Arg Gln Glu Arg Asp Lys Arg
25                  30                  35

Leu Arg Gln Asp Gly Gln Glu Gln Tyr Leu Glu Val
                40                  45

Ala Val Thr Cys Asp Glu Tyr Leu Lys Asp Pro Tyr
50                  55                  60

Ala Asp Pro Ile Val Arg Asp Pro Val Val Arg Glu
                65                  70

Thr Asp Val Phe Ile Ile Gly Gly Gly Phe Gly Gly
                75                  80

Leu Leu Ala Ala Val Arg Leu Gln Gln Ala Gly Val
85                  90                  95

Ser Asp Tyr Val Met Val Glu Arg Ala Gly Asp Tyr
                100                 105

Gly Gly Thr Trp Tyr Trp Asn Arg Tyr Pro Gly Ala
    110                 115                 120

Gln Cys Asp Ile Glu Ser Tyr Val Tyr Met Pro Leu
                125                 130

Leu Glu Glu Met Gly Tyr Ile Pro Thr Glu Lys Tyr
        135                 140

Ala Phe Gly Thr Glu Ile Leu Glu Tyr Ser Arg Ser
145                 150                 155

Ile Gly Arg Lys Phe Gly Leu Tyr Glu Arg Thr Tyr
                160                 165

Phe Gln Thr Glu Val Lys Asp Leu Ser Trp Asp Asp
            170                 175             180

Glu Ala Ala Arg Trp Arg Ile Thr Thr Asp Arg Gly
                185                 190

Asp Lys Phe Ser Ala Arg Phe Val Cys Met Ser Thr
            195                 200

Gly Pro Leu Gln Arg Pro Lys Leu Pro Gly Ile Pro
```

-continued

```
            205                 210                 215
Gly Ile Thr Ser Phe Lys Gly His Ser Phe His Thr
            220                 225
Ser Arg Trp Asp Tyr Ser Tyr Thr Gly Gly Asp Gln
            230                 235                 240
Thr Gly Asn Leu Glu Gly Leu Lys Asp Lys Arg Val
            245                 250
Ala Ile Ile Gly Thr Gly Ala Thr Ser Ile Gln Ala
            255                 260
Val Pro His Leu Ala Ala Tyr Ala Gln Glu Leu Tyr
265                 270                 275
Val Ile Gln Arg Thr Pro Ile Ser Val Gly Phe Arg
            280                 285
Gly Asn Lys Pro Thr Asp Pro Glu Trp Ala Lys Ser
            290                 295                 300
Leu Gln Pro Gly Trp Gln Gln Ala Arg Met Asp Asn
            305                 310
Phe Asn Ala Ile Thr His Gly Met Pro Val Asp Val
            315                 320
Asp Leu Val Gln Asp Ser Trp Thr Lys Ile Phe Gly
325                 330                 335
Glu Ile Gly Val Phe Leu Gly Ser Asp Gly Ser Arg
            340                 345
Ala Gln Met Val Asp Phe Gln Leu Met Glu Gln Ile
            350                 355                 360
Arg Ala Arg Val Asp Gln Glu Val Lys Asp Pro Ala
                    365                 370
Thr Ala Glu Ser Leu Lys Pro Tyr Tyr Asn Ile Met
            375                 380
Cys Lys Arg Pro Gly Phe His Asp Ser Tyr Leu Pro
385                 390                 395
Ser Phe Asn Lys Pro Asn Val Thr Leu Val Asp Thr
            400                 405
Gln Gly Ala Gly Val Glu Arg Ile Thr Glu Lys Gly
            410                 415                 420
Leu Val Val Asn Gly Arg Glu Tyr Glu Val Asp Cys
                    425                 430
Leu Ile Tyr Ala Thr Gly Phe Glu Tyr Gln Thr Lys
            435                 440
Leu Ser Arg Arg Asn Gly Tyr Glu Ile His Gly Arg
445                 450                 455
Asn Gly Gln Pro Leu Ser Asp Lys Trp Lys Asp Gly
            460                 465
Leu Ser Thr Leu Trp Gly Tyr His Ile Arg Asp Phe
            470                 475                 480
Pro Asn Cys Phe Ile Leu Gly Asn Gly Gln Ser Ala
                    485                 490
Val Thr Pro Asn Phe Thr His Met Leu Asn Glu Ala
            495                 500
Gly Lys His Val Ala Tyr Val Val Lys His Cys Leu
505                 510                 515
Asp Glu Arg Val Asp Val Phe Glu Pro Thr Ala Glu
            520                 525
Ala Glu Gln Ala Trp Val Asp His Val Met Ser Phe
            530                 535                 540
Ala Gly Ile Lys Gln Gln Tyr Asp Arg Glu Cys Thr
            545                 550
Pro Ser Tyr Tyr Asn Asn Glu Gly Gln Val Asn Asp
            555                 560
Val Ala Leu Thr Arg Thr Thr Ser Thr Arg Ala Val
565                 570                 575
Arg Ser Leu Ile Asn Ile Leu Arg Glu Trp Arg Glu
            580                 585
Lys Gly Asp Phe Ala Gln Phe Gln Gln Arg Lys Arg
            590                 595                 600
```

The cdnB gene encodes a 600- amino acid residue with an experimentally-determined molecular mass of 66 KDa (FIG. 2).

A notable sequence motif present in CDMO and related proteins is the FAD-binding fingerprint (GXGXXG;) that is similar to those found in flavoprotein hydroxylases.

Comparison of CDMO Activity in *E. coli* and Native HI-70

The CDMO activity from *E. coli* DH5α(pSD-cdnB) was determined to be 0.48 U/mg of protein. This value is approximately three times the value (0.14 U/mg of protein) obtained for the original *P. putida* strain HI-70.

Substrate Specificity of Cloned CDMO:
cyclododecanone (relative activity of 100%)
cyclotridecanone (138%)
cyclopentadecanone (144%)
cycloundecanone (56%)
cyclodecanone (10%)

The activity of CDMO towards alicyclic ketones with small ring members (4 to 9) is relatively insignificant or not detectable. The substrate specificity of the cloned CDMO is identical to that of the native CDMO from *P. putida* strain HI-70.

The specificity spectrum of CDMO towards cyclo-compounds with at least 10-membered rings is a feature that distinguishes this enzyme from any other known BVMOs.

Utility of CDMO Recombinant Biocatalyst in the Industrial Sector

Besides the conventional ketone to lactone biotransformations, BVMOs in general are capable of several heteroatom oxidations. These reactions include sulfo-oxidation, phospho-oxidation, amine oxidation, boron oxidation and seleno-oxidation (Kelly et al. supra; Stewart, supra). For example, the use of BVMOs to perform sulfo-oxidations (sulfides to sulfoxides) has been of considerable interest due to the importance of sulfoxides as chiral auxiliaries in asymmetric synthesis.

In addition to the above-mentioned substrates, the substrate range of CDMO is expected to extend to heteroatom containing compounds. Of particular interest is the production of 15-hexadecanolide, a sex pheromone component of the stink bug, *Piezodorus hybneri* (Kuwahara et al. supra). The latter bug is a notorious pest of legumes such as soybeans and kidney beans. Thus far, 15-hexadecanolide can be synthesized chemically using the Yamaguchi or Mitsunobu macrolactonization reaction of (R)-15-hydroxyhexadecanoic acid prepared from ethyl (R)-beta-hydroxybutyrate in five steps (FIG. 3; Kuwahara et al. supra). A CDMO-catalyzed single reaction step would avoid the use of various solvents and chemicals that are either toxic or "atom-uneconomical", i.e. wasteful. See the comparison in FIG. 3.

Large ring-membered compounds such as cyclododecanone have been described to resemble structures in coal. The bigger the carbon ring, the more flexible it is (remember boat and chair conformations of a cyclic alkane) and more it can take a conformation like that of an open-chain alkane. Specificity of CDMO towards big rings indicate its potential for catalysing attack on aliphatic bridge structures such as those found in coal to generate further value-added products.

The new *Pseudomonas putida* strain HI-70 of the present invention has been deposited at the International Depositary Authority of Canada (National Microbiology Laboratory, Health Canada, Canadian Science Centre for Human and Animal Health, 1015 Arlington St., Suite H3130, Winnipeg, MB R3E 3R2) on Sep. 18, 2002 and was given accession number IDAC-180902.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated cyclododecanone monooxygenase (CDMO) comprising the amino acid sequence as set forth in SEQ ID NO:8.

2. The cyclododecanone monooxygenase (CDMO) of claim 1, wherein said CDMO is prepared from *Psuedomonas putida*.

3. The cyclododecanone monooxygenase (CDMO) of claim 2, wherein said CDMO consists of the sequence as set forth in SEQ ID NO:8.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: Acinobacter sp.
<220> FEATURE:
<221> NAME/KEY: VARIANT
<222> LOCATION: (2)...(2)
<223> OTHER INFORMATION: Xaa = Tyr or His
<220> FEATURE:
<221> NAME/KEY: VARIANT
<222> LOCATION: (5)...(5)
<223> OTHER INFORMATION: Xaa = Arg or Cys
<220> FEATURE:
<223> OTHER INFORMATION: Primer

<400> SEQUENCE: 1

Trp Xaa Trp Asn Xaa Tyr Pro
 1               5

<210> SEQ ID NO 2
<211> LENGTH: 6
<212> TYPE: PRT
<213> ORGANISM: Acinobacter sp.
<220> FEATURE:
<223> OTHER INFORMATION: Primer

<400> SEQUENCE: 2

Ala Thr Gly Phe Asp Ala
 1               5

<210> SEQ ID NO 3
<211> LENGTH: 20
<212> TYPE: DNA
<213> ORGANISM: Artificial Sequence
<220> FEATURE:
<221> NAME/KEY: modified_base
<222> LOCATION: (15)...(15)
<223> OTHER INFORMATION: n = I
<220> FEATURE:
<223> OTHER INFORMATION: Primer

<400> SEQUENCE: 3
tggyaytgga ayhgntaycc                                              20

<210> SEQ ID NO 4
<211> LENGTH: 17
<212> TYPE: DNA
<213> ORGANISM: Artificial Sequence
<220> FEATURE:
```

```
<221> NAME/KEY: modified_base
<222> LOCATION: (9)...(12)
<223> OTHER INFORMATION: n = G, A, T or C
<220> FEATURE:
<221> NAME/KEY: modified_base
<222> LOCATION: (15)...(15)
<223> OTHER INFORMATION: n = I
<220> FEATURE:
<223> OTHER INFORMATION: Primer

<400> SEQUENCE: 4
gcrtcraanc cngtngc                                                  17

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
cggaattcat gagtcagcta attcaagagc                                    30

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
cggaattcaa tcaacgcttg cgctgctg                                      28

<210> SEQ ID NO 7
<211> LENGTH: 1803
<212> TYPE: DNA
<213> ORGANISM: Pseudomonas putida

<400> SEQUENCE: 7
atgagtcagc taattcaaga gccggccgag gctggggtaa cgtcgcagaa agtttccttc     60
gatcatgtgg cgcttcgcga aaatatcgt caggagcgcg acaagcgctt gcgtcaggac    120
ggccaagagc aatatctgga agtcgccgtc acatgtgacg aatacctgaa agaccctat    180 gccgatccga tcgtgcgtga tccggtggtg cgcgagaccg acgtgttcat catcggtggc    240
ggtttcggtg gtctgttggc tgcggtacgc ctgcagcaag caggcgttag cgattatgtg    300
atggttgagc gcgccggtga ctatggcggc acctggtact ggaaccgcta cccgggggcg    360
cagtgcgaca tcgagtcgta tgtctacatg cccttgctcg aagaaatggg ttacataccg    420
accgagaagt acgccttcgg tacgagatc ctcgagtact ccagatcaat cggccgcaaa    480
tttggcttgt acgagcgcac ctacttccag actgaagtga aggatctgag ctgggacgat    540
gaagcggccc gctggcgcat taccaccgac gcggcgaca agttcagcgc gcgcttcgtg    600
tgcatgtcca ccggcccctt gcagcggccc aaactgcccg gcatcccagg tatcacgtcc    660
ttcaagggcc actccttcca caccagtcgc tgggactact cctataccgg cggcgatcag    720
accggcaacc tggaaggttt gaaagacaag cgcgtggcca tcatcggtac cggcgccacc    780
tcaatccagg ctgtgccaca cctggcggcc tatgcccaag agctgtatgt catccagcgc    840
acgccaattt ccgtgggctt ccgtggcaac aagccgactg atcctgaatg ggccaagagc    900
ctgcagccgg gttggcagca agcgcgtatg gacaacttca atgcgatcac ccacggcatg    960
ccggtcgatg tcgatctggt ccaggacagc tggaccaaga tcttcggcga aatcggcgtt   1020
```

-continued

```
tttctgggtt ccgatggcag ccgtgcgcag atggtcgact tccagttgat ggagcaaatc    1080
cgcgcccgcg tcgatcagga agtcaaggat ccggccaccg ctgagtcgct caagccttac    1140
tacaacatca tgtgtaagcg tccgggcttc catgacagtt atctgccctc cttcaacaag    1200
cccaatgtca ccctggtcga tacccaaggc gctggtgttg agcgcatcac cgaaaagggc    1260
ctggtggtca acgccgcga atatgaagtc gactgcctga tctacgccac cggcttcgag    1320
taccagacca agttgtcgcg ccgcaatggc tacgaaatcc acgggcgcaa tggccagccg    1380
ctgagtgaca gtggaaaga cggcctgtcc acactgtggg ctaccacat cgtgacttc      1440 ccgaactgct tcatccttgg caatggtcag tctgcggtaa caccgaactt cactcacatg    1500
ctcaacgaag ctggcaagca tgtggcctat gtggtcaagc actgcctgga cgagcgcgtc    1560
gatgtcttcg agccgaccgc agaggctgag caggcgtggg ttgaccacgt catgtcgttc    1620
gctgggatca agcagcaata cgaccgcgag tgcaccccga gttactacaa caacgaaggc    1680
caggtgaacg acgttgcgct gacccgcaca acttctaccc gggcggtgcg gtcgcttata    1740
aacattctgc gggagtggcg agagaagggc gatttcgcgc agttccagca gcgcaagcgt    1800
tga                                                                 1803
```

<210> SEQ ID NO 8
<211> LENGTH: 600
<212> TYPE: PRT
<213> ORGANISM: Artificial Sequence
<220> FEATURE:
<223> OTHER INFORMATION: Primer

<400> SEQUENCE: 8

```
Met Ser Gln Leu Ile Gln Glu Pro Ala Glu Ala Gly Val Thr Ser Gln
  1               5                  10                  15

Lys Val Ser Phe Asp His Val Ala Leu Arg Glu Lys Tyr Arg Gln Glu
             20                  25                  30

Arg Asp Lys Arg Leu Arg Gln Asp Gly Gln Glu Gln Tyr Leu Glu Val
         35                  40                  45

Ala Val Thr Cys Asp Glu Tyr Leu Lys Asp Pro Tyr Ala Asp Pro Ile
     50                  55                  60

Val Arg Asp Pro Val Val Arg Glu Thr Asp Val Phe Ile Ile Gly Gly
 65                  70                  75                  80

Gly Phe Gly Gly Leu Leu Ala Ala Val Arg Leu Gln Gln Ala Gly Val
                 85                  90                  95

Ser Asp Tyr Val Met Val Glu Arg Ala Gly Asp Tyr Gly Gly Thr Trp
            100                 105                 110

Tyr Trp Asn Arg Tyr Pro Gly Ala Gln Cys Asp Ile Glu Ser Tyr Val
        115                 120                 125

Tyr Met Pro Leu Leu Glu Glu Met Gly Tyr Ile Pro Thr Glu Lys Tyr
    130                 135                 140

Ala Phe Gly Thr Glu Ile Leu Glu Tyr Ser Arg Ser Ile Gly Arg Lys
145                 150                 155                 160

Phe Gly Leu Tyr Glu Arg Thr Tyr Phe Gln Thr Glu Val Lys Asp Leu
                165                 170                 175

Ser Trp Asp Asp Glu Ala Ala Arg Trp Arg Ile Thr Thr Asp Arg Gly
            180                 185                 190

Asp Lys Phe Ser Ala Arg Phe Val Cys Met Ser Thr Gly Pro Leu Gln
        195                 200                 205

Arg Pro Lys Leu Pro Gly Ile Pro Gly Ile Thr Ser Phe Lys Gly His
```

-continued

```
               210                 215                 220
Ser Phe His Thr Ser Arg Trp Asp Tyr Ser Tyr Thr Gly Gly Asp Gln
225                 230                 235                 240

Thr Gly Asn Leu Glu Gly Leu Lys Asp Lys Arg Val Ala Ile Ile Gly
                245                 250                 255

Thr Gly Ala Thr Ser Ile Gln Ala Val Pro His Leu Ala Ala Tyr Ala
            260                 265                 270

Gln Glu Leu Tyr Val Ile Gln Arg Thr Pro Ile Ser Val Gly Phe Arg
        275                 280                 285

Gly Asn Lys Pro Thr Asp Pro Glu Trp Ala Lys Ser Leu Gln Pro Gly
290                 295                 300

Trp Gln Gln Ala Arg Met Asp Asn Phe Asn Ala Ile Thr His Gly Met
305                 310                 315                 320

Pro Val Asp Val Asp Leu Val Gln Asp Ser Trp Thr Lys Ile Phe Gly
                325                 330                 335

Glu Ile Gly Val Phe Leu Gly Ser Asp Gly Ser Arg Ala Gln Met Val
            340                 345                 350

Asp Phe Gln Leu Met Glu Gln Ile Arg Ala Arg Val Asp Gln Glu Val
        355                 360                 365

Lys Asp Pro Ala Thr Ala Glu Ser Leu Lys Pro Tyr Tyr Asn Ile Met
370                 375                 380

Cys Lys Arg Pro Gly Phe His Asp Ser Tyr Leu Pro Ser Phe Asn Lys
385                 390                 395                 400

Pro Asn Val Thr Leu Val Asp Thr Gln Gly Ala Gly Val Glu Arg Ile
                405                 410                 415

Thr Glu Lys Gly Leu Val Val Asn Gly Arg Glu Tyr Glu Val Asp Cys
            420                 425                 430

Leu Ile Tyr Ala Thr Gly Phe Glu Tyr Gln Thr Lys Leu Ser Arg Arg
        435                 440                 445

Asn Gly Tyr Glu Ile His Gly Arg Asn Gly Gln Pro Leu Ser Asp Lys
450                 455                 460

Trp Lys Asp Gly Leu Ser Thr Leu Trp Gly Tyr His Ile Arg Asp Phe
465                 470                 475                 480

Pro Asn Cys Phe Ile Leu Gly Asn Gly Gln Ser Ala Val Thr Pro Asn
                485                 490                 495

Phe Thr His Met Leu Asn Glu Ala Gly Lys His Val Ala Tyr Val Val
            500                 505                 510

Lys His Cys Leu Asp Glu Arg Val Asp Val Phe Glu Pro Thr Ala Glu
        515                 520                 525

Ala Glu Gln Ala Trp Val Asp His Val Met Ser Phe Ala Gly Ile Lys
530                 535                 540

Gln Gln Tyr Asp Arg Glu Cys Thr Pro Ser Tyr Tyr Asn Asn Glu Gly
545                 550                 555                 560

Gln Val Asn Asp Val Ala Leu Thr Arg Thr Thr Ser Thr Arg Ala Val
                565                 570                 575

Arg Ser Leu Ile Asn Ile Leu Arg Glu Trp Arg Glu Lys Gly Asp Phe
            580                 585                 590

Ala Gln Phe Gln Gln Arg Lys Arg
        595                 600
```